United States Patent [19]

Klioze et al.

[11] 4,024,263

[45] May 17, 1977

[54] 1,3-DIHYDROSPIRO[ISOBENZOFURAN-1,4'-PIPERIDINE]S

[75] Inventors: Solomon Samuel Klioze, Flemington; Victor John Bauer, Somerville, both of N.J.

[73] Assignee: American Hoechst Corporation, Bridgewater, N.J.

[22] Filed: Apr. 30, 1975

[21] Appl. No.: 573,145

[52] U.S. Cl. .......................... 424/267; 260/293.58
[51] Int. Cl.$^2$ ...................................... C07D 491/10
[58] Field of Search ................ 260/293.58, 293.66; 424/267

[56] References Cited

UNITED STATES PATENTS 3,745,165  7/1973  Houlihan et al. ............. 260/293.77

OTHER PUBLICATIONS

Roberts, et al., Basic Principles of Org. Chem. (N.Y., 1964), pp. 665–667, 672–673.
Wagner, et al., Synthetic Org. Chem., (N.Y., 1953) pp. 734.
Theilheimer, Syn. Meth. of Org. Chem. (N.Y., 1972) vol. 26, p. 52, No. 88.

Primary Examiner—Cecilia M. S. Jaisle
Attorney, Agent, or Firm—Curtis, Morris & Safford

[57] ABSTRACT

Novel 1,3-dihydrospiro[isobenzofuran-1,4'-piperidine]s and methods of preparing the same are disclosed. These compounds are useful as analgetic, anticonvulsant and antidepressant agents.

13 Claims, No Drawings

1,3-DIHYDROSPIRO[ISOBENZOFURAN-1,4'-PIPERIDINE]S

This invention relates to novel 1,3-dihydrospiro[isobenzofuran-1,4'-piperidine]s which are useful as analgetics and to intermediates therefor, to their pharmaceutically acceptable salts, to methods of preparing the same, to methods of treatment with pharmaceutically effective amounts thereof, and to pharmaceutical compositions containing such compounds as essential ingredients. Additionally, compounds of the invention are useful as anticonvulsants and antidepressants.

To the best of our knowledge, the compounds of this invention have not heretofore been described or suggested. Spiro[phthalan-piperidine]s of the formula

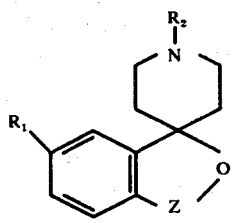

in which $R_1$ is hydrogen, lower alkyl, lower alkoxy, halogen or trifluromethyl, $R_2$ is hydrogen or benzyl, and Z is —$CH_2$— or —CO—, described by W. J. Houhlihan et al. in U.S. Pat. No. 3,686,186, are outside the scope of the invention. The same applies to the natural product of the formula

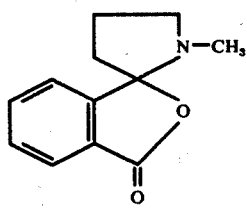

described by Y. Inushubi et al. [Chem. and Pharm. Bull. (Japan), 12, 749 (1964)].

Also outside the scope of this invention are the teachings of V. J. Bauer et al. in U.S. Pat. applications Ser. Nos. 424,080, now U.S. Pat. No. 3,962,259, patented 6/8/76, and 424,117, now abandoned, both filed Dec. 12, 1973.

The compounds of this invention have substantial differences from the compounds of the prior art and exhibit unanticipated pharmacological activity and low toxicity levels.

This invention relates to novel substituted 1,3-dihydrospiro[isobenzofuran-1,4'-piperidine]s of the formulae

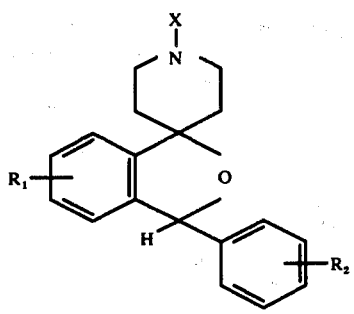

and

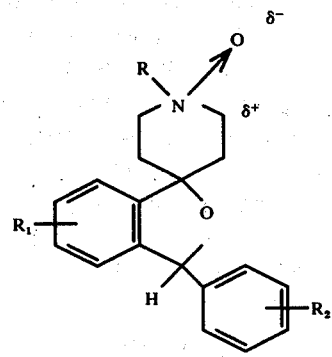

wherein R is alkyl of from 1 to 4 carbon atoms or phenalkyl of from 7 to 9 carbon atoms; X is nitroso, amino, alkylamino of from 1 to 5 carbon atoms, hydroxy or benzoyloxy; $R_1$ is hydrogen alkoxy of 1 to 3 carbon atoms or trifluoromethyl; and $R_2$ is hydrogen, alkoxy of 1 to 3 carbon atoms, bromine, fluorine or chlorine, and to the pharmaceutically acceptable addition salts thereof. The preferred compounds are those wherein X is hydroxy.

Acids useful for preparing the pharmaceutically acceptable acid addition salts of the invention include inorganic acids such as hydrochloric, hydrobromic, sulfuric, nitric, phosphoric, and perchloric acids, as well as organic acids such as tartaric, citric, acetic, succinic, maleic, and fumaric acids.

The compounds of the present invention are prepared by one of the three methods described below from starting piperidines such as those described in U.S. pat. application Ser. No. 424,117. While some compounds of the invention are more active pharmaceutically than others, the less active compounds are nevertheless useful as intermediates for the preparation of the more active compounds.

METHOD A

1. A piperidine of the formula

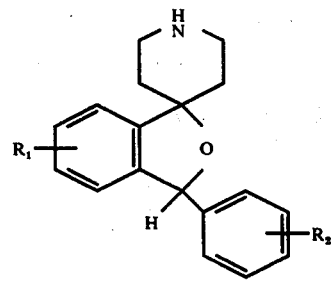

is N-nitrosated by a method known to the art to produce the corresponding nitroso compound of the invention. One preferred method of carrying out the N-nitrosation involves the use of aqueous acetic acid as a solvent and sodium nitrite as a nitrosating salt at a reaction temperature of from about 0° to about 5° C.

2. The above nitroso compound is converted to the corresponding amino compound by a reducing agent, such as elemental zinc, at a temperature of from about 0° to about 110° C (in a solvent such as aqueous acetic acid) for from 5 minutes to two hours.

3. The above amino compound is reductively alkylated for a few minutes to 24 hours at a temperature of from about 15° to about 100° C., with a suitable alkylating and reducing agent in the presence or absence of an organic solvent to produce the corresponding secondary amine, likewise a compound of the invention. One such method involves the use of a carbonyl compound such as a ketone or an aldehyde as the alkylating agent, sodium cyanoborohydride as the reducing agent, and acetonitrile as the solvent.

METHOD B

1. To a cooled solution of benzoylperoxide in a suitable organic solvent such as benzene is added the piperidine, as defined in Method A, step 1, and the mixture is then allowed to react for from a few minutes to 12 hours at about 60° C. to the corresponding N benzoyloxy compound of the invention of the formula

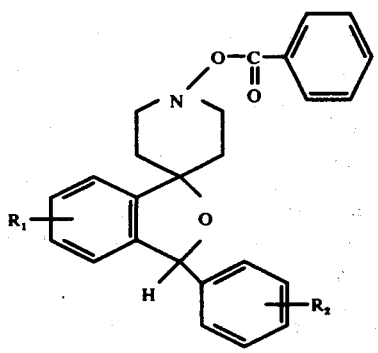

2. The above N-benzoyloxy compound is converted to the corresponding N-hydroxy compound of the invention, preferably by cleaving the benzoyloxy group by treatment with aqueous potassium hydroxide and ethanol and permitting the mixture to react at reflux for from a few minutes to two hours.

METHOD C

A piperidine of the formula

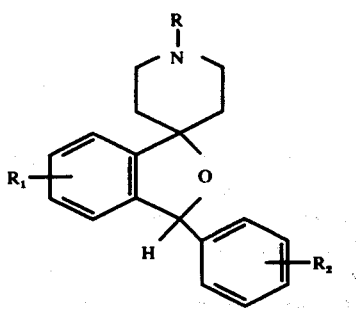

wherein R is alkyl or phenalkyl is oxidized to the corresponding N-oxide of the invention having the formula

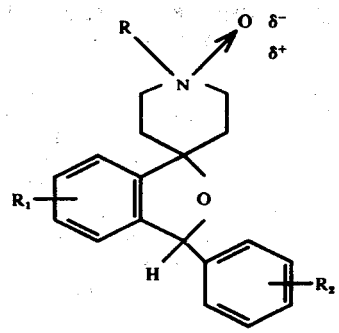

preferably with hydrogen peroxide as the oxidizing agent and an organic solvent at a reaction temperature of about 100° C. for from a few minutes to two hours.

It will be readily appreciated by those skilled in the art that the time and temperature necessary to complete the reaction in the steps of the above methods are interrelated and dependent upon the structures and compositions of the reaction components and the solvent.

The analgetic utility of representative compounds of the invention is demonstrated in the 2-phenyl-1,4-quinone-induced writhing assay in mice, a standard assay for analgesia [Proc. Soc. Exptl. Biol. Med., Vol. 45, 729 (1957)]. Thus, for instance, a 54% inhibition of writhing is effected by a 50 mg/kg of body weight oral dose of 1'-benzoyloxy-1,3-dihydro-3-phenyl-spiro[isobenzofuran-1,4'-piperidine]. Similarly, 50 mg/kg of body weight oral doses of 1'-amino-1,3-dihydro-3-phenylspiro[isobenzofuran-1,4'-piperdine], 1'-hydroxy-1,3-dihydro-3-phenylspiro[isobenzofuran-1,4'-piperidine], 1'-benzyl-1,3-dihydro-3-phenyl-spiro[isobenzofuran-1,4'-piperidine]-1'-oxide, and 1'-(isopropylamino)-1,3-dihydro-3-phenylspiro-[isobenzofuran-1,4'-piperidine] exhibit a 53%, 53%, 48% and 27%, respectively, inhibition of writhing. These data illustrate that the compounds of the invention are useful for the alleviation of pain in mammals when administered in amounts ranging from 1 to about 50 mg/kg of body weight per day.

The antidepressant activity, in mammals, of representative compounds of the invention is demonstrated by their ability to inhibit tetrabenzazine-induced depression in mice [International Journal of Neuropharmacology, Vol. 8, 73 (1969)], a standard assay for useful antidepressant properties, as shown, for example, in Table 1 below. The results are expressed in $ED_{50}$'s (intraperitoneal dose effecting a 50% inhibition of ptosis of tetrabenzazine-induced depression in mice). The doses are in mg/kg of body weight. Table 1 also indicates the low toxicity exhibited by these compounds of the invention. The toxicity data is expressed in $ALD_{50}$'s (the acute lethal intraperitoneal dose, mg/kg of body weight, in 50% of the mice tested). This data was generated by testing groups of four mice at various doses and noting the number of deaths.

TABLE 1

| Compound | Antidepressant $ED_{50}$ | Toxicity $ALD_{50}$ |
| --- | --- | --- |
| 1'-hydroxy-1,3-dihydro-3-phenyl-spiro[isobenzofuran-1,4'-piperidine] | 1.4 | >562 |
| 1'-hydroxy-1,3-dihydro-3-(4-methoxyphenyl)spiro[isobenzofuran-1,4'-piperidine] | 2.6 | >562 |

TABLE 1-continued

| Compound | Antidepressant $ED_{50}$ | Toxicity $ALD_{50}$ |
| --- | --- | --- |
| 1'-hydroxy-1,3-dihydro-6-methoxy-3-phenylspiro[isobenzofuran-1,4'-piperidine] | 3.2 | >562 |
| 1'-hydroxy-1,3-dihydro-3-(4-fluorophenyl)spiro[isobenzofuran-1,4'piperidine] | 4.0 | 316 |
| 1,3-dihydro-1'-methyl-3-phenylspiro[isobenzofuran-1,4'-piperidine]-1'-oxide | 6.5 | 280 |
| 1'-amino-1,3-dihydro-3-phenylspiro[isobenzofuran',4'-piperidine] | 10.3 | 100 |

These data show by way of example the utility of the compounds of the invention for the treatment of depression in mammals when administered intraperitoneally in amounts of ranging from 0.1 to 50 mg/kg of body weight per day.

The compounds of the invention are useful as anticonvulsant agents for mammals, as determined by the method of Woodbury, L. A. and Davenport, V. D., in Arch. Int. Pharmacodynam, Vol. 92, (1952) at pages 97–107. For example, 1'-amino-1,3-dihydro-3-phenylspiro[isobenzofuran-1,4'-piperidine] at an intraperitoneal dose of about 5 mg/kg of body weight produced a 50% protection from the effect of a supra maximal electro shock. This datum illustrates the utility of the compounds of the invention for the treatment of convulsion in mammals when administered in amounts ranging from 0.1 to 50 mg/kg of body weight per day.

Illustrative examples of compounds of the invention are:

5-methoxy-1'-nitroso-1,3-dihydro-3-phenyl-spiro[isobenzofuran-1,4'-piperidine];
1,3-dihydro-1'-methyl-6-trifluromethyl-3-phenyl-spiro[isobenzofuran-1,4'-piperidine]-1'-oxide;
1'-(1-propylamino)-1,3-dihydro-3-phenyl-spiro[isobenzofuran-1,4'-piperidine];
1'-ethylamino-1,3-dihydro-6-methoxy-3-phenyl-spiro[isobenzofuran-1,4'-piperidine];
1'-amylamino-1,3-dihydro-6-methoxy-3-(4-methoxyphenyl)spiro[isobenzofuran-1,4'-piperidine];
1'-butyl-1,3-dihydro-3-phenylspiro[isobenzofuran-1,4'-piperidine]-1'-oxide;
1,3-dihydro-1'-phenethyl-3-phenylspiro[isobenzofuran-1,4'-piperidine]-1'-oxide; and
1'-hydroxy-1,3-dihydro-3-[4-fluorophenyl]-5-methoxyspiro[isobenzofuran-1,4'-piperidine].

Effective quantities of the compounds of the invention may be administered to a patient by any one of various methods, for example, orally as in capsules or tablets, parenterally in the form of sterile solutions or suspensions, and in some cases intraveneously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4 to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches, and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent, and certain preservatives, dyes and colorings, and flavors. Materials used in preparing these various compositions should be pharmaceutically pure and non-toxic in the amounts used.

For the purpose of parenteral therapeutic administration, the active compounds of the invention may be incorporated into solutions or suspensions. These preparations should contain at least 0.1% of active compound, but this may be varied to be between 0.5 and about 30% of the weight thereof. The amount of active compound in such compositions is such that an effective dosage will be obtained. Preferred compositions and preparations according to the present invention are prepared so that parenteral dosage units contain between 0.5 to 100 milligrams of active compound.

The solutions or suspensions may also include the following components: sterile diluents such as water for injection, saline solutions, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in ampules, disposable syringes or multiple dose vials made of glass or plastic.

The invention is further illustrated by the following examples, given for illustrative purposes.

EXAMPLE 1

A solution of 2.1 g of sodium nitrite in 9 ml of water is added dropwise to a stirring solution of 4.0 g of 1,3-dihydro-3-phenylspiro[isobenzofuran-1,4'-piperidine] in 15 ml of glacial acetic acid and 6 ml of water at 0° C. while maintaining the reaction temperature between 0° and 5° C. Upon completion of the addition, the reaction mixture is allowed to stand for one hour at ambient temperature.

Then the reaction mixture is diluted with water, filtered, and the white precipitate is collected, washed with water and cold ethanol and dried. The dried precipitate is recrystallized from ethanol to give very slightly yellow leaflets, mp 159°–161° C., of 1'-nitroso-1,3-dihydro-3-phenylspiro[isobenzofuran-1,4'-piperidine].

Analysis: Calculated for $C_{18}H_{18}N_2O_2$: 73.45%C; 6.16%H; 9.52%N. Found: 73.20%C; 6.11%H; 9.37%N.

EXAMPLE 2

A solution of 7.1 g of 1'-nitroso-1,3-dihydro-3-phenylspiro[isobenzofuran-1,4'-piperidine], Example 1, in 75 ml of glacial acetic is added to a stirring suspension pf 7.1 g of zinc dust in 50 ml of glacial acetic acid and 50 ml of water while maintaining the reaction temperature between 10° and 20° C. The reaction mixture is stirred for 15 minutes at ambient temperature and then at 80° C. for 5 minutes; an additional 4.7 g of zinc dust are introduced and stirring is continued for an additional 10 minutes. The heated mixture is filtered, the precipitate is washed with hot 1N hydrochloric acid and the combined filtrate and washings are basified and extracted with chloroform. The organic solution is dried and the solvent is removed, leaving a white crystalline solid, 1'-amino-1,3-dihydro-3-phenylspiro[isobenzofuran-1,4'-piperidine], which is recrystallized from ethanolto to give the pure product, mp 143°–145° C.

Analysis: Calculated for $C_{18}H_{20}N_2O$: 77.11%C; 7.19%H; 9.99%N. Found: 77.04%C; 7.13%H; 9.69%N.

EXAMPLE 3

0.24 g of sodium cyanoborohydride are added to a mixture of 1.4 g of 1'-amino-1,3-dihydro-3-phenylspiro[isobenzofuran-1,4'-piperidine], Example 2, 25 ml of acetonitrile and 2.5 ml of acetone. Five drops of glacial acetic acid are added and the mixture is warmed briefly and stirred at ambient temperature under nitrogen for five hours while maintaining the pH between 6 and 8. The reaction mixture is then diluted with 250 ml of chloroform, washed with 2N hydrochloric acid and 10% aqueous sodium hydroxide solution and dried. The solvent is removed, leaving a pale yellow oil which upon trituration with an ether-petroleum ether mixture gives a white crystalline solid. The solid is recrystallized from ethanol to give fine white crystals, mp 110°–112° C., of 1'-(isopropylamino)1,3'-dihydro-3-phenylspiro[isobenzofuran-1,4'-piperidine].

Analysis: Calculated for $C_{21}H_{26}N_2O$: 78.22%C; 8.13%H, 8.69%N. Found: 78.03%C; 8.18%H; 8.73%N.

EXAMPLE 4

5.3 g of 1,3-dihydro-3-phenylspiro[isobenzofuran-1,4'-piperidine] are added portionwise to an ice bath cooled solution of 2.4 g of benzoyl peroxide in 75 ml of benzene. The mixture is allowed to react at 60° C. under nitrogen for two hours and the solvent is removed leaving a semi-crystalline residue which is recrystallized from ethanol to give nearly colorless needles, mp 161°–164° C., of 1'-benzoyloxy-1,3-dihydro-3-phenylspiro[isobenzofuran-1,4'-piperidine].

Analysis: Calculated for $C_{25}H_{23}NO_3$: 77.90%C; 6.01%H; 3.63%N. Found: 77.94%C; 6.08%H; 3.64%N.

EXAMPLE 5–7

By following the manipulative procedure described above in Example 4, 1,3-dihydro-3-(4-methoxyphenyl)spiro[isobenzofuran-1,4'-piperidine], 1,3-dihydro-6-methoxy-3-phenylspiro[isobenzofuran-1,4'-piperidine], and 1,3-dihydro-3-(4-fluorophenyl)-spiro[isobenzofuran-1,4'-piperidine] are treated respectively to give the corresponding 1'-benzoyloxy compounds tabulated below in Table II.

TABLE II

| Ex. | Empirical Formula | mp C. | Analysis Calculated | | | | Analysis Found | | | |
|---|---|---|---|---|---|---|---|---|---|---|
| | | | %C | %H | %N | %F | %C | %H | %N | %F |
| 5 | $C_{26}H_{25}NO_4$ | 164–166 | 75.16 | 6.06 | 3.37 | — | 75.14 | 6.22 | 3.34 | — |
| 6 | $C_{26}H_{25}NO_4$ | 163–167 | 75.16 | 6.06 | 3.37 | — | 75.11 | 6.17 | 3.36 | — |
| 7 | $C_{25}H_{22}NO_3F$ | 163–166 | 74.42 | 5.50 | 3.47 | 4.71 | 74.58 | 5.65 | 3.51 | 4.85 |

EXAMPLE 8

A mixture of 2.1 g of 1'-benzoyloxy-1,3-dihydro-3-phenylspiro[isobenzofuran-1,4'-piperidine], Example 4, 24 ml of ethanol and 16 ml of a 10% aqueous sodium hydroxide solution is heated at reflux under nitrogen for 20 minutes. Most of the ethanol is removed in vacuo and the residue is diluted with 40ml of water and the pH is adjusted to 6 by the dropwise addition of 2N hydrochloric acid. The aqueous solution is extracted with chloroform, the combined chloroform extracts are dried, and the chloroform is removed, leaving a pale yellow oil which upon trituration with an ether-petroleum ether mixture gives a white solid. The solid is recrystallized from ethanol to give fine white crystals, mp 184°–187° C. of 1'-hydroxy-1,3-dihydro-3-phenylspiro[isobenzofuran-1,4'-piperidine].

Analysis: Calculated for $C_{18}H_{19}NO_2$: 76.84%C; 6.81%H; 4.98%N. Found: 76.63%C; 6.85%H; 4.80%N.

EXAMPLE 9

A mixture of 1.99 g of 1'-benzoyloxy-1,3-dihydro-3-(4-methoxyphenyl)spiro[isobenzofuran-1,4'-piperidine], Example 5, 24 ml of ethanol and 16 ml of a 10% aqueous sodium hydroxide solution is heated at reflux under nitrogen for 25 minutes. Most of the ethanol is removed in vacuo, the residue is diluted with 40 ml of water and the pH is adjusted to 9 by addition of 2N hydrochloric acid. The aqueous solution is extracted with chloroform, the combined chloroform extracts are dried, and the chloroform is removed, leaving a pale beige solid which upon trituration with an etherpetroleum ether mixture leaves a nearly colorless crystalline solid. The solid is recrystallized from ethanol to give fine white crystals, mp 183°–185° C., of 1'-hydroxy-1,3-dihydro-3-(4-methoxyphenyl)-spiro[isobenzofuran-1,4'-piperidine].

Analysis: Calculated for $C_{19}H_{21}NO_3$: 73.29%C; 6.80%H; 4.50%N. Found: 73.18%C; 6.82%H; 4.48%N.

EXAMPLE 10

A mixture of 1.3 g of 1'-benzoyloxy-1,3-dihydro-6-methoxy-3-phenylspiro[isobenzofuran-1,4'-piperidine], 18 ml of ethanol and 12 ml of 10% aqueous sodium hydroxide solution is heated at reflux under nitrogen for 20 minutes. Most of the ethanol is removed in vacuo, the residue is diluted with 30 ml of water, and the pH adjusted to 8 by addition of 2N hydrochloric acid. The aqueous solution is extracted with chloroform, the combined chloroform extracts are dried, and the chloroform is removed to give a yellow crystalline solid which upon trituration with an ether-petroleum ether mixture leaves a pale yellow crystalline solid. The solid is recrystallized from ethanol to give fluffy white crystals, mp 186°–188° C., of 1'-hydroxy-1,3-dihydro-6-methoxy-3-phenylspiro[isobenzofuran-1,4'-piperidine].

Analysis: Calculated for $C_{19}H_{21}NO_3$: 73.29%C; 6.80%H; 4.50%N. Found: 73.41%C; 6.84%H; 4.46%N.

EXAMPLE 11

By following the manipulative procedure described above in Example 10, the treatment of a mixture of 1.5 g of 1'-benzoyloxy-1,3-dihydro-3-(4-fluorophenyl)-spiro[isobenzofuran-1,4'-piperidine], Example 7, 18 ml of absolute ethanol, and 12 ml of a 10% aqueous sodium hydroxide solution produces fine white crystals, mp 182°–185° C., of 1'-hydroxy-1,3-dihydro-3-(4-fluorophenyl)spiro[isobenzofuran-1,4'-piperidine].

Analysis: Calculated for $C_{18}H_{18}NO_2F$: 72.22%C; 6.06%H; 4.68%N; 6.35%F. Found: 72.20%C; 6.09%H; 4.72%N; 6.15%F.

EXAMPLE 12

A solution of 2.8 g of 1,3-dihydro-1'-methyl-3-phenylspiro[isobenzofuran-1,4'-piperidine], 50 ml of acetic acid and 4 ml of 30% hydrogen peroxide is heated on a steam bath for one hour, diluted with 200 ml of water, concentrated to a total volume of 50 ml, again diluted with 200 ml of water and concentrated to an oil. The oil is dissolved in chloroform, the chloroform solution is washed consecutively with an aqueous sodium bicarbonate solution and water, dried, and the chloroform is removed, leaving an oil which upon trituration with ether gives a solid. The solid is recrystallized from acetonitrile to give colorless crystals, mp 166°–167° C., of 1,3-dihydro-1'-methyl-3-phenyl-spiro[isobenzofuran-1,4'-piperidine]-1'-oxide.

Analysis: Calculated for $C_{19}H_{21}NO_2.H_2O$: 72.83%C; 7.40%H; 4.41%N. Found: 72.00%C; 7.44%H; 4.39%N.

By following the manipulative procedure outlined above, 1,3-dihydro-1'-methyl-6-trifluromethyl-3-phenylspiro[isobenzofuran-1,4'-piperidine] is converted to 1,3-dihydro-1'-methyl-6-trifluoromethyl-3-phenylspiro[isobenzofuran-1,4'-piperidine]-1'-oxide.

EXAMPLE 13

A solution of 2.0 g of 85% 3-chloroperbenzoic acid in 25 ml of chloroform is added dropwise to a stirring solution, chilled to 0° C. under nitrogen, of 3.6 g of 1'-benzyl-1,3-dihydro-3-phenylspiro[isobenzofuran-1,4'-piperidine] in 15 ml of chloroform. After total addition the resulting solution is stirred for three hours at ambient temperature, diluted with 50 ml of chloroform, washed with a saturated aqeous sodium bicarbonate solution and the chloroform is removed in vacuo, leaving a very pale yellow oil. The oil is triturated with an ether-petroleum ether mixture to give a white crystalline solid which is recrystallized from acetonitrile to give a somewhat hygroscopic white crystalline solid, mp 147°–150° C., of 1'-benzyl-1,3-dihydro-3-phenylspiro[isobenzofuran-1,4'-piperidine]-1'-oxide.

Analysis: Calculated for $C_{25}H_{25}NO_2$: 80.83%C; 6.78%H; 3.77%N. Found: 80.65%C; 6.84%H; 3.73%N.

We claim:

1. A compound of the formula

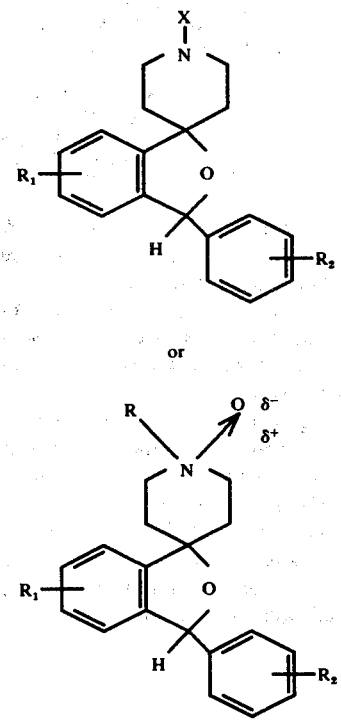

or

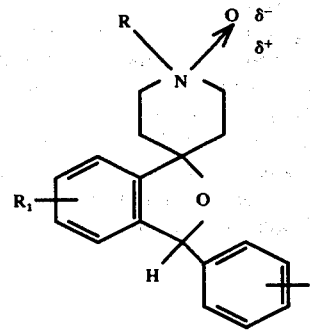

wherein R is alkyl of from 1 to 4 carbon atoms or phenalkyl of from 7 to 9 carbon atoms; X is nitroso, amino, alkylamino of from 1 to 5 carbon atoms, hydroxy, or benzoyloxy; $R_1$ is hydrogen, alkoxy of from 1 to 3 carbon atoms or trifluoromethyl; $R_2$ is hydrogen, alkoxy of from 1 to 3 carbon atoms, bromine, fluorine or chlorine; or a pharmaceutically acceptable acid addition salt thereof.

2. The compound as defined in claim 1 of the formula

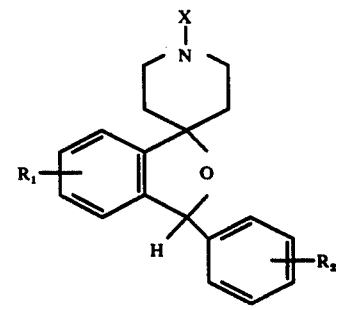

wherein X is nitroso, amino, akylamino of from 1 to 5 carbon atoms; hydroxy or benzoyloxy; $R_1$ is hydrogen or methoxy; and $R_2$ is hydrogen, methoxy or fluorine.

3. The compound as defined in claim 1 of the formula

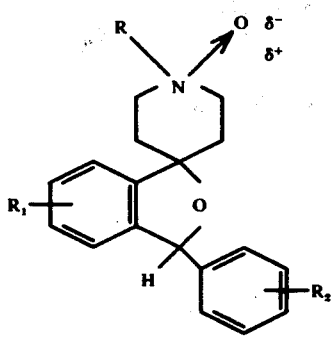

wherein R is alkyl of 1 to 4 carbon atoms, benzyl or phenethyl, $R_1$ is hydrogren or methoxy; and $R_2$ is hydrogen, methoxy or fluorine.

4. The compound as defined in claim 1 which is 1'-hydroxy-1,3-dihydro-3-phenylspiro[isobenzofuran-1,4'-piperidine] or a pharmaceutically acceptable acid addition salt thereof.

5. The compound as defined in claim 1 which is 1'-hydroxy-1,3-diydro-3-(4-methoxyphenyl)spiro[isobenzofuran-1,4'-piperidine] or a pharmaceutically acceptable acid addition salt thereof.

6. The compound as defined in claim 1 which is 1'-hydroxy-1,3-dihydro-6-methoxy-3-phenylspiro[isobenzofuran-1,4'-piperidine] or a pharmaceutically acceptable acid addition salt thereof.

7. The compound as defined in claim 1 which is 1'-hydroxy-1,3-dihydro-3-(4-fluorophenyl)spiro[isobenzofuran-1,4'-piperidine] or a pharmaceutically acceptable acid addition salt thereof.

8. The compound as defined in claim 1 which is 1'-amino-1,3-dihydro-3-phenylspiro[isobenzofuran-1,4'-piperidine] or a pharmaceutically acceptable acid addition salt thereof.

9. The compound as defined in claim 1 which is 1,3-dihydro-1'-methyl-3-phenylspiro[isobenzofuran-1,4'-piperidine]1'-oxide.

10. A method of alleviating pain which comprises administering to a patient in need of such treatment a pharmaceutically effective amount of a compound as defined in claim 1.

11. A method of treating convulsions which comprises administering to a patient in need of such treatment a pharmaceutically effective amount of a compound as defined in claim 1.

12. A method of treating depression which comprises administering to a patient in need of such treatment a pharmaceutically effective amount of a compound as defined in claim 1.

13. A pharmaceutical composition for alleviating pain, treating convulsions or treating depression which comprises between about 0.5 and about 70 percent by weight of a compound as defined in claim 1 as the essential active ingredient, the balance being a pharmaceutically acceptable carrier therefor.

* * * * *